United States Patent [19]
Afeyan et al.

[11] Patent Number: 5,376,249
[45] Date of Patent: Dec. 27, 1994

[54] ANALYSIS UTILIZING ISOELECTRIC FOCUSING

[75] Inventors: Noubar B. Afeyan, Brookline, Mass.; Fred E. Regnier, West Lafayette, Ind.

[73] Assignee: PerSeptive Biosystems, Inc., Cambridge, Mass.

[21] Appl. No.: 981,814

[22] Filed: Nov. 25, 1992

[51] Int. Cl.⁵ .............................................. B01D 57/02
[52] U.S. Cl. ............................ 204/180.1; 204/182.8; 204/182.9; 204/183.2; 204/299 R; 436/517
[58] Field of Search ............... 204/182.8, 182.9, 183.2, 204/299 R, 180.1; 436/517

[56] References Cited

U.S. PATENT DOCUMENTS

| | | | |
|---|---|---|---|
| 3,692,654 | 9/1972 | Svendsen | 204/180 R |
| 4,102,990 | 7/1978 | Uzigris | 424/12 |
| 4,181,589 | 1/1980 | Brooks | 204/180 R |
| 4,198,389 | 4/1980 | Wadsworth | 424/8 |
| 4,264,327 | 4/1981 | Blum | 23/230 B |
| 4,628,035 | 12/1986 | Tokinaga et al. | 436/518 |
| 4,853,335 | 8/1989 | Olsen et al. | 436/527 |
| 4,936,974 | 6/1990 | Rose et al. | 204/299 R |
| 4,939,098 | 7/1990 | Suzuki et al. | 436/514 |
| 5,045,172 | 9/1991 | Guzman | 204/299 R |
| 5,057,438 | 10/1991 | Imai et al. | 436/516 |
| 5,061,361 | 10/1991 | Gordon | 204/299 R |
| 5,084,150 | 1/1992 | Karger et al. | 204/180.1 |
| 5,116,471 | 5/1992 | Chien et al. | 204/180.1 |
| 5,122,248 | 6/1992 | Karger et al. | 204/182.8 |
| 5,137,609 | 8/1992 | Manian et al. | 204/180.1 |
| 5,145,567 | 9/1992 | Hsieh et al. | 204/180.1 |

FOREIGN PATENT DOCUMENTS

| | | |
|---|---|---|
| 57-026751A | 2/1982 | Japan . |
| WO91/06850 | 5/1991 | WIPO . |

OTHER PUBLICATIONS

Karger et al., *Journal of Chromatography*, 492:585–614 (1989).
Nielsen et al., *Journal of Chromatography*, 539:177–185 (1991).
Deutscher, Ed., *Methods in Enzymology*, Academic Press, Inc., San Diego, Calif., 182:459–477, Ch. 35 (1990).
Duetscher, Ed., *Methods in Enzymology*, Academic Press, Inc., San Diego, Calif., 182:477–488, Ch. 36 (1990).
Foret, et al., *Electrophoresis*, 11:661–664 (1990).
Novotny, et al., *Electrophoresis*, 11:735–749 (1990).
Wang et al., "Whole Column Absorbance in Capillary Isoelectric Focusing", *Anal. Chem.*, 64:1745–1747 (1992).
Zhu et al., "Optimizing Separation Parameters in Capillary Isoelectric Focusing", *Journal of Chromatography*, 559:479–488 (1991).

*Primary Examiner*—John Niebling
*Assistant Examiner*—C. Delacroix-Muirheid
*Attorney, Agent, or Firm*—Testa, Hurwitz & Thibeault

[57] ABSTRACT

Disclosed are methods and apparatus for determining the presence of one or more analytes in a sample, wherein the presence of a complex of an analyte and an analyte-specific binding moiety is detected at a location in an elongate pH gradient corresponding to a predetermined isoelectric point of the complex in the gradient. An electric field applied across the elongate pH gradient prior to the detection of the complex transports the complex to the location in the pH gradient corresponding to the predetermined isoelectric point. The analyte-specific binding moiety preferably is provided with a detectable label such as a fluorescent label. A parameter, e.g., fluorescence intensity, indicative of the amount of the complex at the location in the pH gradient corresponding to the predetermined isoelectric point may be determined to quantitate the analyte.

26 Claims, 2 Drawing Sheets

ANALYSIS UTILIZING ISOELECTRIC FOCUSING

FIELD OF THE INVENTION

This invention relates to methods for the detection of an analyte in a sample utilizing isoelectric focusing techniques.

BACKGROUND OF THE INVENTION

Isoelectric focusing is an electrophoretic technique wherein an electric field is applied to a molecule in a pH gradient to mobilize the molecule to a position in the pH gradient at which its net charge is zero, i.e., the isoelectric point of the molecule. It often is used to separate proteins in a mixture and as an aid in characterization of biomolecules of unknown composition. Commercially available gradients may be utilized in isoelectric focusing which consist of multicharged ampholytes, with closely spaced pI values and high conductivity, which partition into a pH gradient upon application of an electric field. The ampholytes are generally provided in a support matrix, such as a polyacrylamide gel. Molecules separated by isoelectric focusing may be visualized, e.g., by silver staining or Coomassie blue staining. Deutscher, Ed., *Methods in Enzymology*, Vol. 182, Academic Press, Inc., San Diego, Calif., 1990, Chapter 35.

Capillaries have been used in various electrophoretic techniques including isoelectric focusing. Novotny et al., *Electrophoresis*, 11:735-749 (1990). U.S. Pat. No. 5,061,361 (1991) relates to a capillary electrophoresis system in which a nanoliter volume of sample is introduced into the capillary tube, and an electric field is imposed on the system to effect separation of the charged components. After migration along the length of the tube, the sample components are detected via ultra-violet absorbance. U.S. Pat. No. 5,084,150 (1992) relates to an electrokinetic separation in which the surface of moving charged colloidal particles is treated so as to interact selectively with the sample molecules to be separated. An electric field is imposed on a capillary tube containing the colloidal particles and the sample to achieve separation. U.S. Pat. No. 5,045,172 (1991) relates to a capillary electrophoresis apparatus in which electrodes are attached at each end of a capillary tube, and a detector is coupled to the tube. U.S. Pat.. No. 4,181,589 (1980) relates to a method for separating biological cells using an electric field.

A wide range of specific binding assays, such as immunoassays, have been described in the prior art (see Bolton et al., *Handbook of Experimental Immunology*, Weir, D. M., ed., Blackwell Scientific Publications, Oxford, 1986, Vol. 1, Chapter 26, for a general discussion on immunoassays.) Antibody-antigen complexes have been resolved by isoelectric focusing in the prior art. Nielsen et al., *J. Chromatography*, 539:177-185 (1991). Japanese Patent Application No. 57026751 discloses the detection of an antigen-antibody complex using isoelectric focusing, wherein either the antigen or the antibody is chemically bound to a solid particle.

SUMMARY OF THE INVENTION

The invention provides methods and apparatus for determining the presence of an analyte in a sample, wherein the presence of a complex of the analyte and an analyte-specific binding moiety is detected at a location in an elongate pH gradient corresponding to a predetermined isoelectric point of the complex in the pH gradient. An electric field is applied across the elongate pH gradient containing the complex, prior to detection of the complex, to transport the complex by electromotive force to the location in the pH gradient corresponding to the predetermined isoelectric point.

The complex in the gradient may be detected visually or by utilizing any of a number of spectrophotometric methods, such as detecting UV absorption of the complex, or other methods available in the art. In preferred embodiments, a parameter indicative of the amount of the complex at the isoelectric point may be determined, to quantitate the analyte. The sample containing the analyte and the binding moiety may be added separately to the pH gradient prior to the application of the electric field, and the analyte and the binding moiety may be allowed to complex within the pH gradient upon the application of the electric field. Alternatively, the binding moiety may be added to the sample to form the complex prior to the addition of the sample to the pH gradient.

In preferred embodiments, the analyte-specific binding moiety includes a label detectable at the location in the gradient corresponding to the isoelectric point of the complex, and which also may be used to quantitate the analyte. The detectable label may comprise, e.g., a fluorescent, radioactive, phosphorescent or colored particle label. The labeled complex may be detected visually or with a spectrophotometer or other detector. In a preferred embodiment, the label may comprise a fluorescent label, which may be detected by focusing electromagnetic radiation selectively at the location in the pH gradient corresponding to the known isoelectric point of the labeled complex, and detecting fluorescence emission of the labeled complex using a spectrophotometer or a spectrofluorometer. This advantageously localizes fluorescence at the predetermined isoelectric point of the complex in the gradient.

The binding moiety may comprise a member of any of a range of possible ligand-receptor specific binding pairs known in the art. A ligand-receptor pair is defined herein as any pair of molecules capable of specific binding interactions, including antibody-antigen, enzyme-substrate, nucleic acid-nucleic acid, protein-nucleic acid and other specific binding pairs known in the art. The binding moiety may comprise an antibody or a truncated fragment thereof, e.g., a monovalent binding protein such as an Fab fragment. The binding moiety also may comprise a biosynthetic single chain binding molecule of the type known in the art. By selecting the appropriate binding moiety, any analyte may be detected, providing only that it is immunogenic, or that an analyte specific binding moiety selectively reactive with the analyte is known or can be produced using known technologies. Various components in a biological fluid sample may be detected, such as enzymatic, hormonal, genetic, viral or other components.

In another embodiment, plural analytes in a single sample may be detected in a single pH gradient. In this embodiment, plural complexes, each comprising an analyte and an analyte-specific binding protein, are detected at a location corresponding to the isoelectric point of each complex in the pH gradient, and an analyte-specific binding protein is provided for each analyte in the sample.

The elongate pH gradient typically is disposed within means defining an elongate channel, such as an elongate capillary. Longer gradients are preferred in many cases as they provide better discrimination among complexes with close pIs. In many embodiments, the pH gradient may be a shallow gradient, preferably a long, shallow gradient extending, e.g., only a fraction of a pH unit about the predetermined pI of the complex. This permits resolution of the complex of the binding moiety with the specific analyte of interest spatially from complex with a species present in the sample cross reactive with the binding moiety and having a similar pI. Other charged species having pIs outside the gradient are transported rapidly to the poles of the imposed electric field and are eliminated from the assay. In a further embodiment, a bundle of capillaries may be provided, to permit analytes to be detected in plural samples in plural capillaries simultaneously. After each assay, the pH gradient may be expelled from within the capillary or other channel, and a new pH gradient may be delivered to the channel for a subsequent assay, thus allowing the channels to be reused.

In the embodiment where the pH gradient is housed within a capillary, the presence or measure of the amount of the complex at the isoelectric point may be detected utilizing any of a range of possible detection methods available in the art, such as by whole capillary detection, i.e., by inserting the entire capillary into a detector. The pH gradient may be moved past a detector, e.g., by electrophoretic transport. Alternatively, an elongate channel, such as a capillary containing the gradient may be moved past a detector, such as a spectrophotometer, or the detector may be transported along the length of the pH gradient. The use of a capillary provides improved and faster separation, since higher voltages may be utilized during isoelectric focusing due to the enhanced capacity of the capillary to dissipate heat.

The methods and apparatus of the invention are advantageous because the complex of the analyte and the binding protein conveniently migrates to a unique isoelectric point thereby separating the analyte from other components in the sample. An additional advantage of the invention is that non-specific binding by the binding protein, a major source of error and constraint on sensitivity in many conventional immunoassay formats, will not influence the accuracy of the assay, because any complex produced by non-specific binding will migrate to a different point in the gradient than the pI of the analyte-binding protein complex being detected. The methods and apparatus of the invention may be utilized either or both qualitatively and quantitatively to rapidly detect one or a plurality of analytes in a single or plural separate gradients. The invention can be adapted easily for automated analysis, can be designed to detect essentially any analyte, and requires only very small quantities of reagents. By combining the discriminating power of a specific binding protein, isoelectric focusing of a complex, and modern spectrophotometry techniques, one can obtain high levels of sensitivity and reproducibility.

BRIEF DESCRIPTION OF THE DRAWINGS

Like reference characters in the respective drawn Figures indicate corresponding parts.

DETAILED DESCRIPTION

A. General Discussion

The invention provides methods and apparatus for determining the presence of an analyte in a sample, wherein a complex of the analyte and an analyte-specific binding moiety is detected at a location in an elongate pH gradient corresponding to a predetermined isoelectric point of the complex. An electric field applied across the elongate pH gradient prior to the detection of the complex transports the complex by electromotive force to the location in the pH gradient corresponding to its isoelectric point. The binding moiety may be contacted with the sample suspected to contain the analyte to form the complex, and then the complex may be delivered to the elongate pH gradient. Alternatively, the sample and the binding protein may be added separately to the elongate pH gradient prior to the application of the electric field, to allow the binding protein and analyte to contact and form a complex at a time after the electric field is applied.

Figure 6:
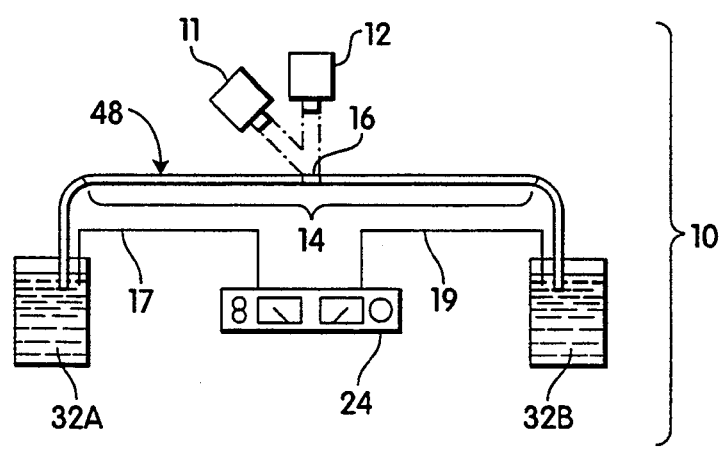
FIG. 6 is a longitudinal, partially cross-sectional schematic view of an apparatus 10 which includes an elongate pH gradient 14, housed within capillary 48, and means 12 for detecting a complex of an analyte and an analyte specific binding moiety at the location 16 in gradient 14 corresponding to the isoelectric point of the complex.

The method and apparatus may be understood best with reference to FIG. 6, which shows a capillary 48 in fluid communication with buffer reservoirs 32A and 32B which can be maintained at a negative and positive polarity, respectively, by voltage source 24 connected to electrodes 17 and 19. Also illustrated in FIG. 6 is a light source 11 focused to a predetermined location along the capillary 48, here illustrated as zone 16, to induce fluorescence of a fluorescent tag on the analyte-binding moiety complex, at the isoelectric point of the complex located within zone 16. The fluorescence of the fluorescent tag on the complex is detected in zone 16 by detector 12, and provides a positive indication of the presence of the analyte in a sample. Capillary 48 contains conventional buffer fluid and a pH gradient of the type commonly used in isoelectric focusing procedures, illustrated at 14. The range of pH values of gradient 14 should embrace the pI of the complex used to detect the analyte.

The binding protein preferably is labeled to facilitate detection and/or quantitation of the complex. While the label can take many forms as discussed below, in this explanation, a fluorescent moiety of the type known per se and commonly used in immunoassay procedures is employed. Thus, for example, an FAB' antibody fragment specific for the analyte labeled with, e.g., fluorescein, is reacted with an authentic sample of the analyte to form a fluorescein-labeled complex. The location in the gradient corresponding to the isoelectric point of the labeled complex then is determined. After determination of the isoelectric point of the complex, the labeled binding moiety is reacted with a sample suspected to contain the analyte. This step is done in solution either prior to the introduction of sample or complex into the apparatus, in a chamber disposed adjacent the mouth of the capillary, or directly within the capillary itself. In the latter case a "plug" of labeled binding protein may be disposed within the lumen of the capillary, e.g., after the pH gradient is established, which upon introduction of a given volume of the sample, will react with the sample in situ.

Gradient 14 may be established using reagents known in the art and available commercially. The reagents essentially are polymers comprising various amounts of hydrogen donating and hydrogen accepting groups which, in the presence of a charge gradient, migrate to their pIs, i.e., the point between the positive and negative poles where their net charge is zero.

Labeled complex formed inside or outside of the capillary, when introduced into the capillary, migrates electrophoretically through the pH gradient, exchanging hydrogen ions with its environment as it moves, until it reaches the pH in which the net charge on the complex is zero, i.e., until the complex reaches its pI. Its position in the capillary therefore will be at the pH within the gradient wherein the complement of hydrogen ions induces a net balance of positive and negative charges on the complex. This pI will be unique for a given complex, as pI is a characteristic property of a chemical species. The position of the complex in the gradient at the pI therefore is reproducible and predetermined, and it is at this pI where one looks to read out the data determinative of the presence, and optionally and preferably, the concentration of the analyte, as shown in FIG. 6.

To conduct a quantitative analysis, one employs the apparatus of FIG. 6 first to determine the pI of a complex comprising at least the analyte and an analyte-specific binding protein, and then to prepare a standard curve correlating strength of the fluorescence signal to analyte concentration using samples of known analyte concentration. The standard curve, which correlates a signal intensity of the complex (in this example, fluorescence intensity) to analyte concentration, is thereafter used to determine the concentration of the analyte in a sample of unknown analyte concentration. The concentration of the analyte can be determined rapidly and with precision by assaying the sample of unknown analyte concentration using a protocol similar to that employed in generating the standard curve and comparing the fluorescence, if any, at the predetermined pI, to the standard curve, directly or indirectly.

Non-specific interaction between the analyte-specific binding moiety and chemical species other than the analyte are a significant source of error in conventional immunoassays, and often is determinative of the sensitivity of the assay. In the isoelectric focusing assay, as should be apparent from the explanation set forth above, a complex of the binding moiety with a species other than the analyte will have a pI different from the complex of the analyte and accordingly will be displaced from position 16, can be distinguished from the true complex by position, and will not contribute to background. If, in a given analysis, fluorescence is detected only at a location significantly different from position 16, then the tester knows that analyte, if present, is present at a concentration below the level of sensitivity of the test. Similarly, fluorescence from uncomplexed, labeled binding protein can be distinguished readily and not confused with the signal from the complex.

Because the isoelectric focusing and the reactions can be implemented in elongate pH gradients of very low volume, such as in the capillary described above, only very small quantities of reagents and test sample are required. Furthermore, in configurations exploiting capillaries, the surface area to volume ratio of the gradient can be quite high, and therefore heat generated when using large voltage gradients can be dissipated easily. This means that the isoelectric focusing assays can be conducted rapidly, i.e., in a few minutes or seconds.

The methods and apparatus of the invention also may be utilized to detect multiple analytes in a single sample in a single pH gradient disposed within an elongate channel, such as an elongate capillary. In this embodiment, plural analyte-specific binding moieties are provided in the pH gradient, each specific for an analyte to be detected in the sample. The isoelectric point of each complex of analyte and analyte-specific binding moiety is predetermined. Upon addition of a sample and the binding moieties to the gradient, the presence of plural spaced apart complexes is detected in the gradient, wherein each complex comprises an analyte and an analyte-specific binding moiety, at the predetermined isoelectric point of each complex. The binding moieties and the sample may be added to the gradient either separately or after formation of the complexes. Thus, in one pH gradient, several analytes in one sample may be detected. In an assay for multiple analytes in a single gradient, it is only necessary that each complex of analyte and analyte-specific binding moiety having a unique and distinguishable isoelectric point in the gradient.

The process and apparatus of the invention may be embodied in many specific forms and various aspects of these forms are described below.

B. pH Gradients

Isoelectric focusing methods generally known and available in the art may be applied to the practice of this invention. Commercially available pH gradients may be utilized which consist of mixtures of ampholytes, preferably with closely spaced pI values and high conductivity, and which partition into smooth pH gradients upon application of an electric field. The carrier ampholytes may be provided in a polyacrylamide gel support matrix, e.g., in an elongate horizontal slab gel. Additionally, such products are available having a buffering capacity adequate to maintain local pH during passage of the sample containing the analyte, the binding moiety, and the complex. Ampholytes available in the art may be utilized which may comprise, e.g., amphoteric polymers with varying amounts of amino and carboxylate groups, which can provide a resolution of approximately 0.02 pH units, and are available in narrow and wide pH ranges. Deutscher, Ed., *Methods in Enzymology*, Vol. 182, Academic Press, Inc., San Diego, Calif., 1990, Chapter 35. Ampholytes are available from commercial suppliers, such as Bio-Rad, Cambridge, Mass.

Preferred pH gradients are disposed in a capillary of glass, plastic, or other material, or in a suitable substrate machined to define a narrow, elongate channel, and capable of dissipating heat. Shallow gradients, e.g., gradients whose ΔpH is relatively small per unit length, e.g., 1.0 pH unit/10 cm, or 0.1 pH unit/10 cm, often are preferred as they permit resolution of complexes having similar pI. pH gradients which span, e.g., less than 2.0 pH units may be utilized. Such gradients permit resolution among members of a family of closely related chemical structures such as isomers, or protein species varying in amino acid sequence or post translational processing. The gradients can be prepared readily by, for example, fractionating conventional ampholytes to obtain preparations within a narrow pH range by chromatography or other means. It is also often advantageous to prepare the gradient so that its ends revert to regions of constant pH over length, fairly close to the predetermined pI of the complex. For example, a gradient for detecting a complex of pI 8.2 may extend from pH 7.7 to pH 8.7 over, e.g., five centimeters. This design variable can be exploited to effect elimination of charged species in the sample having a pI outside the gradient, which species rapidly migrate to the poles.

C. The Binding Moiety-Analyte Complex

The binding moiety-analyte complex may comprise any amphoteric complex, carrying positive, negative or zero charges, depending on the pH of the local environment, and which, upon application of an electric field, is transported by electromotive force to a predetermined location in an elongate pH gradient corresponding to the isoelectric point of the complex in the gradient, i.e., the pH in the gradient at which the overall charge on the complex is zero. In one embodiment the binding moiety and/or the analyte may comprise, e.g., an amphoteric protein containing ionizable acidic and basic side chains of its constituent amino acids and prosthetic groups. The binding moiety and/or the analyte also may comprise other molecules capable of forming an amphoteric complex such as, but not limited to, e.g., a nucleic acid, a phospholipid or a polysaccharide.

Analytes which may be detected in a sample include, but are not limited to components of a biological fluid sample such as a protein, e.g., a hormone, cytokine, lymphokine or enzyme, or a drug, nucleic acid, polysaccharide, or lipid. In a preferred embodiment, such analytes may be quantitated as described herein.

The binding moiety and the analyte each constitute one member of a ligand-receptor pair, which is defined as any pair of molecules capable of specific binding interactions. Thus either the binding moiety or the analyte may comprise, e.g., a member of a binding pair such as an antibody-antigen, enzyme-substrate, hormone-receptor, nucleic acid-binding protein, or nucleic acid-nucleic acid pair, or other specific binding pairs known in the art. In a preferred embodiment, a monovalent binding moiety with high binding specificity for the analyte is utilized. The appropriate binding moiety may be selected based on the choice of analyte to be detected.

In one example, the analyte and/or the binding moiety may comprise a nucleic acid. To detect a nucleic acid fragment of a specific molecular weight in a sample, a binding moiety may be selected which comprises a second nucleic acid, or a protein, capable of specifically binding the nucleic acid constituting the analyte. The nucleic acid constituting the analyte may comprise, e.g., a restriction enzyme fragment of naturally occurring polynucleotide, or a synthetic polynucleotide fragment. Thus, a nucleic acid in a sample can be rapidly detected and/or quantitated using the appropriate labeled or unlabeled binding moiety. In another embodiment, an analyte comprising a protein, such as an enzyme or an antibody in a sample, may be detected by selecting a binding moiety which comprises a nucleic acid, optionally labeled, capable of specifically binding the protein constituting the analyte.

D. Antibodies and Synthetic Antibody Fragments

To detect an analyte, such as a protein, in a sample, one may employ a binding moiety comprising an antibody, for example a monoclonal antibody (mAb), capable of specifically binding the analyte. Techniques for the manufacture of antibodies are known to those skilled in the art. The use of a monovalent antibody enhances the specificity of the assay. A monovalent antibody advantageously binds only to a single epitope and therefore generally a single molecule of the antigen constituting the analyte. Thus multiple binding of the analyte to the antibody is substantially prevented.

In the instance where the binding moiety constitutes a bivalent antibody, a 2:1 complex of the analyte and the antibody can form in the presence of excess analyte. However, in contrast to conventional immunoassays, the formation of a 2:1 complex of analyte and antibody will not interfere with the accuracy of the assay, because the 2:1 complex will have a separate characteristic isoelectric point in the pH gradient distinguishable from the isoelectric point of the 1:1 complex. In the assay, the location in the pH gradient corresponding to the isoelectric point of both the 1:1 and the 2:1 complex of the analyte and the antibody may be predetermined and the presence of a complex at either or both locations may serve as a positive indicator of the presence and/or concentration of the analyte in the sample, or as a control.

To avoid multiple binding of the analyte to the antibody, a monovalent antibody such as an Fab antibody fragment may be utilized. Alternatively, genetically engineered biosynthetic antibody binding sites may be utilized which comprise either 1) non-covalently associated or disulfide bonded synthetic $V_H$ and $V_L$ dimers, 2) covalently linked $V_H$-$V_L$ single chain binding sites, 3) individual $V_H$ or $V_L$ domains, or 4) single chain antibody binding sites as disclosed, for example in Huston et al., U.S. Pat. Nos. 5,091,513 (1992) and 5,132,405 (1992), and in Ladner et al., U.S. Pat. Nos. 4,704,692 (1987) and 4,946,778 (1990), the disclosures of which are incorporated herein by reference.

E. Detection of the Analyte-Binding Moiety Complex

The binding moiety-analyte complex may be detected at its isoelectric point in the elongate pH gradient, e.g., by detecting UV absorbance of the complex, or by staining the complex in the gradient with an organic dye, such as Coomassie blue, or by silver staining. Naturally colored complexes containing visually detectable chromophores may be detected by illumination with light in the visual spectrum. Generally, methods for the detection of proteins resolved in isoelectric focusing gradients previously developed in the art are operative. Deutscher, Ed., *Methods in Enzymology*, Vol. 182, Academic Press, Inc., San Diego, Calif., 1990, Chapter 36.

The detection of the complex may be implemented e.g., visually, or using a detector such as a spectrophotometer or other detector suitable for the complex being detected. The detector may be positioned to detect selectively the location in the pH gradient corresponding to the isoelectric point of the complex, thus enhancing the accuracy of the assay.

F. Detectable Labels

In a preferred embodiment, the binding moiety is provided with a detectable label, which facilitates detection and quantitation of the complex at the location in the gradient corresponding to the predetermined isoelectric point. The detectable label may comprise, e.g., a fluorescent, phosphorescent, radioactive, enzymatic, or colored organic or inorganic particle label. The label may be detected, e.g., visually or by using a spectrophotometer or other detection means available in the art. In one embodiment, a fluorescent label on the binding moiety in the complex may be detected using a detecting means such as a spectrophotometer or a spectrofluorimeter which measures absorbance at a preselected wavelength, e.g., 495 nm. The fluorescent label also may comprise a fluorescent moiety capable of being detected by time-resolved fluorescence. A fluorescence detector focused on the location in the pH gradient corresponding to the isoelectric point of the complex eliminates stray, nonspecific fluorescence in the gradient. The use of fluorescent labels in detecting targeted substances in electrophoretic systems is described, e.g., in U.S. Pat. No. 5,137,609 (1992). The amount of label detected at the location in the pH gradient corresponding to the isoelectric point of the complex also may be correlated with a standard created with known concentrations of the analyte, thereby to quantitate the analyte.

The label on the binding moiety also may comprise a colored particle label, such as colloidal gold. Protein labeling with colloidal gold has been described in the prior art, e.g., in U.S. Pat. No. 4,853,335 (1989). The label on the binding moiety also may comprise colored particles used in the prior art as marker substances in immunoassays as described, e.g., in Leuvering, U.S. Pat. No. 4,313,734 (1982). Additionally, colored particle conjugates, such as those described in Horisberger, *Biol. Cellulaire*, 36, 253–258 (1979); Leuvering et al., *J. Immunoassay*, 1:77–91 (1980); and Frens, *Nature, Physical Science*, 241:20–22 (1973) are available. Gold and other polymeric or inorganic particle labels may be detected visually or by X-ray absorption or using any of a range of other detection methods available in the prior art.

When the binding moiety is labeled, the assay typically will produce at least two labeled species in the pH gradient, corresponding to the free and complexed labeled binding moiety in the gradient. The presence of free labeled binding moiety in the pH gradient at its isoelectric point can conveniently provide a positive control for the assay. Non-specifically bound species comprising the labeled binding moiety also may be present in the gradient. In the embodiment where the binding moiety is a labelled bivalent antibody, in the presence of excess analyte, a labeled 2:1 complex of the analyte and the antibody, the labeled 1:1 complex, and the free labeled binding moiety all may be apparent. However, in the assay, the additional labeled species in the gradient each will migrate to a different characteristic isoelectric point and therefore will not interfere with the accuracy of the assay. Additionally, a detector may be positioned to detect specifically the absorbance, emission or other detectable signal of the labeled complex selectively at the location in the gradient corresponding to the isoelectric point of the complex.

G. Quantitation of the Analyte

In a preferred embodiment, the analyte is quantitated utilizing the assay methods and apparatus of the invention. A standard plot can be produced correlating a detectable parameter of the complex at the isoelectric point in the gradient with known concentrations of the analyte. Thereafter, the presence and concentration of the analyte in a sample of unknown analyte concentration can be determined rapidly and with precision by running the unknown using a protocol similar to that employed in generating the standard plot.

The standard plot may be created, e.g., by correlating UV absorbance of the labeled or unlabeled complex with analyte concentration. Additionally, the absorbance of a complex stained with an inorganic or organic dye may be correlated with analyte concentration. Methods for the quantitation of proteins resolved in isoelectric focusing gradients using silver and organic dyes developed in the art may be utilized. Deutscher, Ed., *Methods in Enzymology*, Vol. 182, Academic Press, Inc., San Diego, Calif., 1990, Chapter 36.

Other parameters may be utilized to create a standard plot. The strength of a detectable signal of a label on the complex, such as fluorescence emission, radioactivity, X-ray absorption or other possible detectable signals may be correlated with analyte concentration to create a standard plot. Thus, a parameter representative of the amount of the complex at the location in the pH gradient corresponding to the isoelectric point may be determined, to quantitate the analyte. The output of this assay may be compared to a standard, to obtain quantitative data directly or indirectly. For example, in an analysis device dedicated to rapid detection of a given analyte in successive samples, the level of successive readings may be converted to electronic signals, which are compared electronically to stored data correlating output to analyte concentration.

H. Capillary Electrophoresis

In a preferred embodiment, the elongate pH gradient is disposed within means defining an elongate channel, such as a capillary, for example with a diameter less than about 500 microns. Methods of capillary isoelectric focusing are described in the prior art e.g., in Karger et al., *J. Chromatography*, 492:585–614 (1989); and Novotny et al., Electrophoresis 11:735–749 (1990). The capillary tube may be modified with a coating, such as a neutral hydrophilic polymer, to reduce electroosmotic flow, and to maintain reproducibility. The separated complex may be eluted from the capillary by pressurized flow or may be mobilized from the capillary by electrophoretic transport by the addition of a salt to the anolyte or the catholyte, which causes positive ions of the salt to exchange with protons in the capillary generating a pH imbalance gradient to elute the complex from the tube. The complex may be eluted at a predetermined time past a detector.

The capillary tube may be reusable. The use of a bundle of capillaries allows plural samples to be assayed simultaneously. The use of a capillary, which has a high capacity for dissipating heat, allows higher voltages to be used, which improves and accelerates resolution of the complex at its isoelectric point. In conventional isoelectric focusing, electric fields on the order of 100 V/cm are generally used, whereas in capillary isoelectric focusing, electric fields on the order of 200-500 V/cm may be used.

Surfactants and hydrophilic polymers also may be adsorbed to octadecyl silane derivatized capillaries, to reduce electro-osmotic flow and the adsorption of proteins, and to enable isoelectric focusing and electrophoretic mobilization to occur in one step, as described in Yao and Regnier, "Polymer and Surfactant Coated Capillaries for Isoelectric Focusing."

The detection of the complex at the location corresponding to the isoelectric point in a pH gradient disposed within an elongate channel may be conducted by moving a detector along the gradient, or by moving the channel containing the gradient past a detector. The complex may be detected by whole capillary detection, i.e., by inserting the whole capillary in a detector. The complex also can be detected by moving the pH gradient, disposed within an elongate channel, past a detector, e.g., by electrophoretic transport, as described above. The detector may comprise, e.g., a spectrophotometer or other detection means, depending on the choice of binding moiety and analyte.

I. Apparatus

Figure 1:
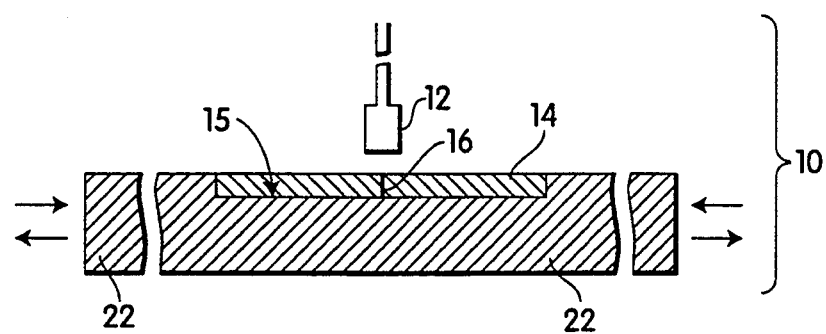
FIG. 1 is a longitudinal, partially cross-sectional schematic view of an apparatus 10 which includes an elongate pH gradient 14 and means 12 for detecting the complex of an analyte and an analyte-specific binding moiety at the location 16 in the gradient 14 corresponding to the isoelectric point of the complex.

FIG. 1 illustrates schematically an apparatus 10 comprising a structure used to implement the assay of the invention. The apparatus comprises an elongate pH gradient 14, disposed within an elongate channel 15, formed within a substrate 22. A detecting means 12, e.g., a fluorimeter, is disposed in optical communication with the gradient 14, and detects the presence of the complex of an analyte and an analyte specific binding moiety at a location 16 corresponding to the isoelectric point of the complex in the gradient 14.

Figure 2:
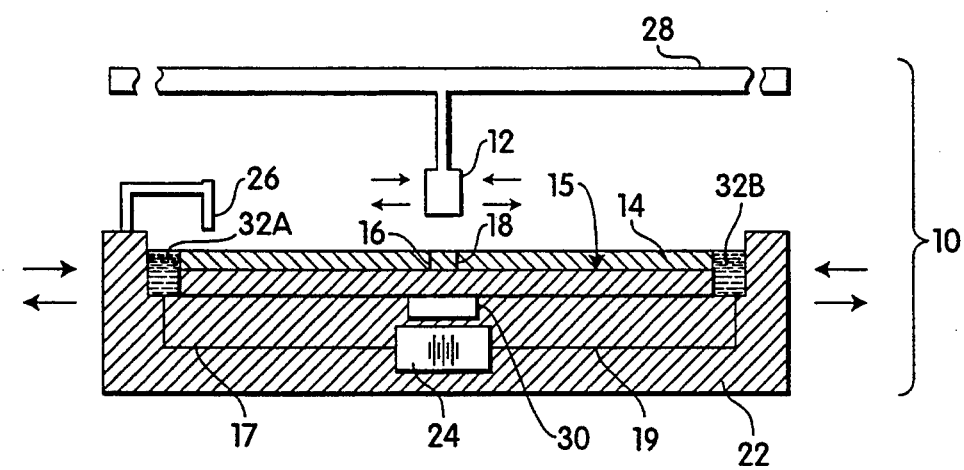
FIG. 2 is a longitudinal, partially cross-sectional schematic view of an apparatus 10 which includes a voltage source 24 for applying an electric field to an elongate pH gradient 14 and means 12 for detecting a complex of an analyte and an analyte-specific binding moiety in the location 16 in the pH gradient 14 corresponding to the isoelectric point of the complex.

In the embodiment of FIG. 2, the apparatus 10 includes a voltage source 24 for applying an electric field to the pH gradient 14, to transport the complex to the location 16 in the pH gradient 14 corresponding to its isoelectric point. Voltage source 24 is connected at the cathode and anode ends via electrodes 17 and 19 to buffer solutions 32A and 32B. In the embodiment of FIG. 2, the apparatus further includes a delivery means 26, which delivers a sample suspected to contain the analyte to the pH gradient 14. The delivery means 26 also may be used to deliver the binding moiety, optionally labeled, to the pH gradient. Alternatively, a complex of the analyte and the binding moiety may be delivered using delivery means 26. Delivery means 26 may be used to deliver the binding moiety, the sample, or the complex to any location in the gradient, prior to application of an electric field. It can be embodied as a micropipette serviced by a pump or as many other means known to the art of microsampling and automated analysis.

Figure 3:
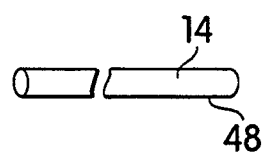
FIG. 3 is a schematic perspective view of a pH gradient 14 housed within a capillary 48.
Figure 4:
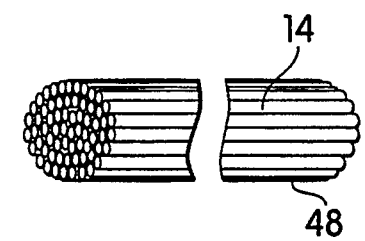
FIG. 4 is a schematic perspective view of pH gradients 14 disposed within a bundle 50 of capillaries 48.
Figure 5:
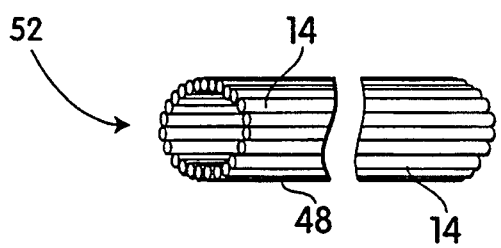
FIG. 5 is a schematic perspective view of pH gradients 14 disposed within a bundle 52 of capillaries 48 with a cavity at the center of the bundle.

Apparatus 10 in FIG. 2 also includes an elongate channel 15 housing the pH gradient 14, which in a preferred embodiment comprises a capillary, such as is schematically illustrated in FIG. 3 at 48. Alternatively, as illustrated in FIG. 4, the apparatus may include a bundle 50 of capillaries 48, wherein each capillary includes a pH gradient 14, and detector 12 may comprise means for detecting an analyte from a sample in each capillary, thereby allowing a plurality of samples to be assayed simultaneously. Alternatively, a bundle 52 of capillaries 48 may be structured with a cavity at the center as shown in FIG. 5, allowing a detector or an activating light to be inserted within the central cavity.

The detecting means 12 in apparatus 10 in FIGS. 1 and 2 may comprise any device known in the art capable of detecting an unlabeled or labeled complex in pH gradient 14. Detector 12 may comprise, e.g., means for detecting a complex comprising a fluorescent, phosphorescent, radioactive, or colored particle label. In one embodiment, means 12 may comprise means such as a spectrophotometer for detecting, e.g., UV absorbance or X-ray absorbance of the complex in the gradient 14. In another embodiment, detecting means 12 may comprise a spectrofluorometer, for detecting a fluorescently labeled complex. Detector 12 also preferably includes means for measuring a parameter proportional to the amount of the labeled or unlabeled complex at the isoelectric point in the gradient, that is, a means for measuring the intensity of the optical or other signal, so as to permit a measure of the amount of analyte present at the focus point.

Detector 12 also may be used to detect a plurality of spaced-apart complexes. In FIG. 2, detector 12 may be utilized to detect two complexes of an analyte and a binding moiety at the locations 16 and 18 in the gradient 14, corresponding to the isoelectric points of each complex. Thus plural analytes in a sample can be detected in a single gradient 14 by providing a binding moiety in the gradient for each analyte, and then detecting and/or measuring the intensity of the signal at each predetermined isoelectric point. Detector 12 may be moved, in one embodiment, to scan the pH gradient along guide 28 in FIG. 2. Alternatively, substrate 22 may be transported together with elongate channel 15, past detector 12.

In still another embodiment, neither the capillary or other structure holding the gradient nor the detector need be moved. Rather, once the complex is focused, the entire gradient may be transported within the capillary so that the focused complex moves past the detector. Transport can be induced by pumping fluid through the capillary to convectively move the gradient downstream, or by electrokinetic transport. In any embodiment where the plug or zone of complex is moved relative to the detector, the predetermined pI will remain constant, but the physical position of the focused complex will shift. It is accordingly preferred to standardize flow rates or to provide other design features which seek to maximize exploitation of the inherent advantages of the invention provided by the electrophoretic separation of species. Thus, for example, in a device where the whole gradient is moved, the detector may be programmed to take a reading only at a predetermined time after the start of flow, a time determined to coincide with passage of the analyte complex.

Further embodiments are within the following claims.

What is claimed is:

1. A method for determining the presence of an analyte in a sample comprising the step of:
   detecting the presence of an amphoteric complex of an analyte and an analyte-specific binding moiety at a location in an elongate pH gradient corresponding to a predetermined isoelectric point of the complex in the pH gradient, thereby to determine the presence of the analyte in a sample.

2. The method of claim 1 comprising the additional step of:
   applying an electric field across the elongate pH gradient, containing the complex, prior to said detecting step, thereby to transport the complex by electromotive force to the location in the pH gradient corresponding to the predetermined isoelectric point.

3. The method of claim 1 comprising the additional step of:
determining a parameter indicative of the amount of the complex at the location in the pH gradient corresponding to the predetermined isoelectric point, thereby to quantitate the analyte.

4. The method of claim 1 wherein plural analytes are detected in a sample, said detecting step further comprising:
detecting in the elongate pH gradient the presence of plural, spaced apart complexes, each complex comprising an analyte and an analyte-specific binding moiety, at a location in the pH gradient corresponding to a predetermined isoelectric point of each complex in the pH gradient.

5. The method of claim 1 wherein the analyte-specific binding moiety comprises a detectable label, and
wherein said detecting step comprises detecting the label in the complex at the location in the pH gradient corresponding to the isoelectric point of the complex.

6. The method of claim 5 wherein the detectable label is selected from the group consisting of a fluorescent label, a phosphorescent label, a radioactive label and a colored particle label.

7. The method of claim 6 wherein the label is a fluorescent label, and wherein said detecting step comprises:
focusing fluorostimulating electromagnetic radiation selectively at the location in the pH gradient corresponding to the isoelectric point of the labeled complex, and
detecting fluorescent emission by the label in the complex at the location in the pH gradient corresponding to the isoelectric point, thereby to indicate the presence of the analyte in the sample.

8. The method of claim 5 comprising the additional step of:
detecting a parameter proportional to the amount of the label at the location in the pH gradient corresponding to the isoelectric point of the complex, thereby to quantitate the analyte.

9. The method of claim 1 wherein the analyte-specific binding moiety and the analyte are members of a complementary ligand-receptor pair.

10. The method of claim 9 wherein the binding moiety is selected from the group consisting of a protein and a nucleic acid.

11. The method of claim 9 wherein the binding moiety is selected from the group consisting of a bivalent antibody and a monovalent antibody.

12. The method of claim 9 wherein the binding moiety is a biosynthetic single chain binding molecule.

13. The method of claim 2 comprising, prior to said applying step, the additional steps of:
contacting the binding moiety with a sample suspected to contain the analyte, thereby to form the complex, and
delivering the complex to the elongate pH gradient.

14. The method of claim 2, comprising, prior to said applying step, the additional step of:
delivering a sample suspected to contain the analyte and the binding moiety separately to the elongate pH gradient, and
wherein the binding moiety contacts the analyte to form the complex within the elongate pH gradient after initiation of said applying step.

15. The method of claim 1 wherein the pH gradient comprises ampholytes defining a substantially continuous pH gradient, capable of buffering the sample containing the analyte and the binding moiety.

16. The method of claim 2 wherein the elongate pH gradient is disposed within means defining an elongate channel.

17. The method of claim 16 wherein said detecting step is conducted by moving a detector along the pH gradient.

18. The method of claim 16 wherein said detecting step is conducted by moving the pH gradient past a detector.

19. The method of claim 18 wherein the pH gradient is moved by electrophoretic transport.

20. The method of claim 16 wherein the means defining an elongate channel comprises a capillary.

21. The method of claim 20 wherein said detecting step is conducted by moving the capillary past a detector.

22. The method of claim 20 wherein the capillary has a diameter less than about 500 microns.

23. The method of claim 20 further comprising, after said detecting step, the steps of:
removing the pH gradient from the capillary,
adding a new pH gradient to the capillary, and
repeating said applying and detecting steps, thereby to reuse the capillary.

24. The method of claim 20 wherein said detecting step is conducted by whole capillary detection.

25. The method of claim 16 wherein the presence of an analyte in plural samples is detected;
wherein the means defining an elongate channel further defines plural elongate channels, each channel comprising a pH gradient; and
wherein the detecting step comprises detecting the presence of the complex in a pH gradient for each sample.

26. The method of claim 25 wherein each channel comprises a capillary.

* * * * *